United States Patent [19]

Draber et al.

[11] Patent Number: 4,489,085

[45] Date of Patent: Dec. 18, 1984

[54] ANTIMICROBIAL AGENTS AND THEIR USE EMPLOYING IMIDAZOLYL-ENAL ETHERS

[75] Inventors: Wilfried Draber; Karl H. Büchel; Manfred Plempel; Ingo Haller, all of Wuppertal, Fed. Rep. of Germany

[73] Assignee: Bayer Aktiengesellschaft, Leverkusen, Fed. Rep. of Germany

[21] Appl. No.: 172,331

[22] Filed: Jul. 25, 1980

[30] Foreign Application Priority Data

Aug. 4, 1979 [DE] Fed. Rep. of Germany ....... 2931778

[51] Int. Cl.³ .................. A61K 31/415; A61K 31/555
[52] U.S. Cl. .................................... 424/273 R; 424/245
[58] Field of Search ........................... 424/245, 273 R

[56] References Cited

U.S. PATENT DOCUMENTS

| | | | |
|---|---|---|---|
| 3,912,752 | 10/1975 | Meiser et al. | 548/269 |
| 4,130,409 | 12/1978 | Shephard et al. | 548/262 |
| 4,203,995 | 5/1980 | Funaki et al. | 424/273 R |

FOREIGN PATENT DOCUMENTS

| | | | |
|---|---|---|---|
| 2331 | 6/1979 | European Pat. Off. | 548/262 |
| 2671 | 7/1979 | European Pat. Off. | 548/262 |

*Primary Examiner*—Allen J. Robinson
*Attorney, Agent, or Firm*—Sprung Horn Kramer & Woods

[57] ABSTRACT

The invention relates to the provision of antibacterial compositions and medicaments (as well as methods for their use as antibacterials) containing as an active compound an imidazolylenol ether of Formula (I) as defined hereinbelow.

3 Claims, No Drawings

ANTIMICROBIAL AGENTS AND THEIR USE EMPLOYING IMIDAZOLYL-ENAL ETHERS

The present invention relates to the use as antimicrobial agents of certain imidazolyl-enol ethers which are novel.

It has already been disclosed that imidazolyl ethers, such as substituted 3,3-dimethyl-1-(imidazol-1-yl)-1-phenoxy-2-(R-oxy)-butanes, have good antimycotic properties (see DE-OS (German Published Specification) No. 2,720,868 corresponding to U.S. Ser. No. 897,900 filed Apr. 18, 1978, now U.S. Pat. No. 4,233,311 dated Nov. 11, 1980). However, the action of these compounds is not always completely satisfactory.

According to the present invention there are provided pharmaceutical composition containing as an active ingredient a compound which is an imidazolyl-enol ether of the formula

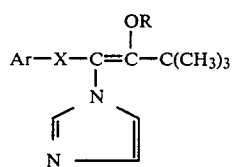

(I)

and/or a physiologically acceptable acid addition salt and/or metal salt complex thereof, in which
  Ar represents an optionally substituted aryl radical,
  R represents an alkyl radical and
  X represents an oxygen atom or a methylene radical,
in admixture with an inert pharmaceutical carrier, such as a solid or liquefied gaseous diluent or in admixture with a liquid diluent other than a solvent of molecular weight less than 200 except in the presence of a surface-active agent. The pharmaceutical compositions of the present invention have good antimicrobial properties, in particular antimycotic properties.

The compounds of the formula (I) to be used according to the invention can exist in the form of the geometric isomers E(trans) and Z(cis). In the E,Z nomenclature, the substituents located on the double bond are arranged in decreasing priority in accordance with the Cahn-Ingold-Prelog rule. If the preferred substituents are located on the same side of the double bond, the isomer has the Z (derived from zusammen (together) configuration, and if they are on opposite sides, the isomer has the E(derived from entgegen (opposite)) configuration. Both the individual isomers and the mixtures are claimed according to the invention.

Surprisingly, the imidazolyl-enol ethers of the formula (I) which can be used according to the invention exhibit a better antimycotic activity than the imidazolyl ethers which are known from the state of the art and are closely related compounds chemically and from the point of view of their action. The substances which can be used according to the invention thus represent an enrichment of pharmacy.

Particularly preferred imidazolyl-enol ethers used according to the invention are those in which Ar represents an aryl radical (preferably mono- or bi-cyclic carbocyclic) which has 6 to 10 carbon atoms (preferably phenyl or naphthyl) and is optionally monosubstituted or polysubstituted (e.g. di- or tri-substituted, etc.) by identical or different substituents, preferred substituents being: halogen (especially fluorine, chlorine or bromine); alkyl with 1 to 6 (preferably 1 to 4) carbon atoms; alkoxy with 1 to 4 (preferably 1 or 2) carbon atoms; halogenoalkyl with 1 to 4 carbon atoms and 1 to 5 halogen atoms (preferably with up to 2 carbon atoms and up to three identical or different halogen atoms, halogens being, preferably fluorine and chlorine); nitro; cyano; or phenyl which is optionally substituted by halogen (preferably chlorine), R represents a straight-chain or branched alkyl radical with 1 to 4 carbon atoms and X represents an oxygen atom or a methylene radical.

Very particularly preferred imidazolyl-enol ethers used according to the invention are those in which Ar represents a phenyl radical which is optionally mono-substituted or disubstituted by identical or different substituents selected from halogen (preferably fluorine, chlorine, bromine or iodine), alkyl with 1 to 3 carbon atoms (preferably methyl, ethyl or isopropyl), trifluoromethyl, nitro, phenyl and chlorophenyl; R represents an alkyl radical with 1 to 4 carbon atoms (preferably a methyl, ethyl, isopropyl, isobutyl or tert.-butyl radical); and X has the meaning indicated above.

The following compounds of the formula (1) may be mentioned specifically, in addition to the compounds mentioned in the preparation examples:

$$\underset{\substack{\mid\\ N\\ \diagdown\diagup\\ N}}{\text{Ar}-\text{X}-\text{C}}\overset{\text{OR}}{\underset{}{=}}\underset{}{\text{C}}-\text{C}(\text{CH}_3)_3 \quad (I)$$

| Ar | X | R |
|---|---|---|
| Cl–⟨phenyl⟩– | O | CH$_3$ |
| Cl–⟨phenyl⟩– | O | i-C$_3$H$_7$ |
| Cl–⟨phenyl⟩– | O | i-C$_4$H$_9$ |
| Cl–⟨phenyl⟩– | CH$_2$ | CH$_3$ |
| Cl–⟨phenyl⟩– | CH$_2$ | C$_2$H$_5$ |
| Cl–⟨phenyl⟩– | CH$_2$ | i-C$_3$H$_7$ |
| Cl–⟨phenyl⟩– | CH$_2$ | i-C$_4$H$_9$ |
| Cl–⟨phenyl⟩–⟨phenyl⟩– | CH$_2$ | CH$_3$ |
| Cl–⟨phenyl⟩–⟨phenyl⟩– | CH$_2$ | C$_2$H$_5$ |
| Cl–⟨phenyl(Cl)⟩– | O | CH$_3$ |

-continued $$\text{Ar} - X - \underset{\underset{\underset{N}{\Vert}}{N}}{C} = \underset{OR}{\overset{OR}{C}} - C(CH_3)_3 \quad (I)$$

| Ar | X | R |
|---|---|---|
| 2,4-dichlorophenyl | O | $C_2H_5$ |
| 2,4-dichlorophenyl | $CH_2$ | $CH_3$ |
| 2,4-dichlorophenyl | $CH_2$ | $C_2H_5$ |
| 4-fluorophenyl | O | $CH_3$ |
| 4-fluorophenyl | O | $C_2H_5$ |
| 4-fluorophenyl | $CH_2$ | $CH_3$ |
| 4-fluorophenyl | $CH_2$ | $C_2H_5$ |
| 4-chloro-2-methylphenyl | O | $CH_3$ |
| 4-chloro-2-methylphenyl | O | $C_2H_5$ |
| 4-chloro-2-methylphenyl | $CH_2$ | $CH_3$ |
| 4-chloro-2-methylphenyl | $CH_2$ | $C_2H_5$ |
| 3-methylphenyl | O | $CH_3$ |
| 3-methylphenyl | O | $C_2H_5$ |
| 3-methylphenyl | $CH_2$ | $CH_3$ |
| 3-methylphenyl | $CH_2$ | $C_2H_5$ |
| 4-nitrophenyl | O | $CH_3$ |
| 4-nitrophenyl | O | $C_2H_5$ |
| 4-nitrophenyl | $CH_2$ | $CH_3$ |
| 4-nitrophenyl | $CH_2$ | $C_2H_5$ |
| 2-methylphenyl | O | $CH_3$ |
| 2-methylphenyl | O | $C_2H_5$ |
| 2-methylphenyl | $CH_3$ | $CH_3$ |
| 2-methylphenyl | $CH_3$ | $C_2H_5$ |
| 4-biphenylyl | O | $CH_3$ |
| 4-biphenylyl | O | $C_2H_5$ |
| 4-biphenylyl | $CH_2$ | $CH_3$ |
| 4-biphenylyl | $CH_2$ | $C_2H_5$ |

The active compounds to be used according to the invention, and acid addition salts and metal salt complexes thereof are novel. However, they can be prepared as described in our copending application Ser. No. 170,276 filed July 17, 1980 (German application No. P 29 31 665, Le A 19 816), by reacting an imidazolyl ketone of the formula

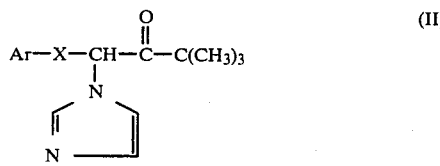

in which

Ar and X have the meaning indicated above, with an alkyl (preferably $C_1$-$C_6$-alkyl) sulphate, such as, dimethyl sulphate or diethyl sulphate, or alkyl (preferably $C_1$-$C_6$-alkyl) halide, preferably an alkyl bromide and iodide, in the presence of an inert organic solvent, such a dimethylsulphoxide, at temperatures between 0° to 100° C.

In a preferred embodiment, this reaction is carried out in a two-phase system, such as aqueous alkali metal hydroxide solution, such as a sodium hydroxide solution or potassium hydroxide solution/toluene or methylene chloride, if appropriate with the addition of 0.1-1 mole of a phase transfer catalyst, such as, ammonium or phosphonium compounds, benzyl-dodecyl-dimethyl-ammonium chloride (Zephirol) and triethyl-benzyl-ammonium chloride being mentioned as examples (see also the preparative Examples).

The compounds of the formula (I) are obtained in the form of the geometric isomer mixtures. Isolation of the individual geometric isomers is effected in the customary manner, for example, on the basis of different solubility, by salt formation, by Craig distribution or by chromatographic processes, or by a combination of these methods. An unambiguous allocation of the structure is effected on the basis of the $^1$H-NMR data, in particular using shift reagents.

The imidazolyl ketones of the formula (II) are known (see DE-AS (German Published Specification) No. 2,105,490 corresponds to U.S. Pat. Nos. 3,812,142 and 3,903,287 dated May 21, 1974 and Sept. 2, 1975, respectively and DE-OS (German Published Specification) No. 2,638,470 corresponding to U.S. Pat. No. 4,079,143 dated Mar. 14, 1978), and they can be obtained by the processes indicated in these Specifications, for example by reacting corresponding halogenoketones with imidazole in the presence of a diluent and in the presence of an acid-binding agent.

The alkyl sulphates and halides also required as starting substances for the process according to the invention are generally known compounds of organic chemistry.

The following acids can preferably be used for the preparation of physiologically acceptable acid addition salts of the compounds of the formula (I): the hydrogen halide acids, (such as hydrobromic acid and preferably hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicyclic acid, sorbic acid and lactic acid) and sulphonic acids (such as p-toluenesulphonic acid and 1,5 naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV of sub-groups I and II and IV to VIII can be used for the preparation of metal salt complexes of the compounds of the formula (I), examples of metals which may be mentioned being copper, zinc, manganese, magnesium, tin, iron and nickel.

Possible anions of the metal salt complexes are those which, preferably, are derived from the same acids as those mentioned above as preferably for the preparation of physiologically acceptable acid-addition salts and include the following acids: hydrogen halide acids (such as, hydrochloric acid and hydrobromic acid), phosphoric acid, nitric acid and sulphuric acid.

The metal salt complexes of compounds of the formula (I) can be obtained in a simple manner by customary processes, thus, for example, by dissolving the metal salt in alcohol (for example ethanol), and adding this solution to the compound of the formula (I). The metal salt complexes can be purified in a known manner, for example by filtration, isolation and, if appropriate, by recrystallization.

The compounds of the formula (I) which can be used according to the invention, and their acid addition salts and metal salts complexes, display antimicrobial actions, in particular powerful antimycotic actions. They possess a very broad antimycotic action spectrum, especially against dermatophytes and blastomyces a well as biphase fungi, for example against varieties of Candida, such as Candida albicans, varieties of Epidermophyton, such as Epidermophyton floccosum, varieties of Aspergillus, such as Aspergillus niger and Aspergillus fumigatus, varieties of Trichophyton, such as Trichophyton mentagrophytes, varieties of Microsporon, such as Microsporon felineum and varieties of Penicillium, such as Penicillium commune. The listing of these micro-organisms in no way implies a limitation of the germs which can be combated but is merely illustrative.

The compounds of the formula (I) and their salts can be used in medicine. The term "pharmaceutical composition" includes compositions adapted for administration to warm-blooded animals. Such compositions are preferably prepared free from pathogenic microorganisms which could be harmful to warm-blooded animals and include a sterile pharmaceutical carrier.

Examples which may be mentioned of fields of indication in medicine are: dermatomycoses and systemic mycoses caused by Trichophyton mentagrophytes and other varieties of Trichophyton, varieties of Microsporon, Epidermophytan fluoccosum, blastomyces and biphase fungi as well as moulds.

As stated above, the invention also relates to the use in medicine of the compounds of the invention.

The present invention provides pharmaceutical compositions containing as active ingredients a compound of the invention in admixture with an inert pharmaceutical carrier, such as a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosols sprays, can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g., ethyoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceuticals compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with an inert carrier or in the form of a medicament according to the invention.

It is envisaged that these active compounds will be administered perorally, parenterally (for example intramuscularly, intraperitoneally), subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the in vivo and in vitro activity of the compounds used according to the present invention.

EXAMPLE A

Antimycotic in vitro Activity

Description of the experiment:

The in vitro test was carried out in a series dilution test using germ inocula of an average $5 \times 10^4$ germs/ml of substrate. The nutrient medium used was (a) for dermatophytes and moulds: Sabouraud's milieu d'épreuve, and (b) for yeasts: isotonic sensitest broth from Oxid.

The incubation temperature was 18° C.; the duration of incubation was 24 hours in the case of yeasts and 96 hours in the case of dermatophytes and moulds.

In this experiment, the compounds according to the invention exhibit very good minimum inhibitory concentration values.

EXAMPLE B

Antimicrobial in vivo Activity (Oral) in Candidosis of Mice

Description of the experiment:

Mice of the SPF-CF$_1$ type were infected intravenously with $1-2 \times 10^6$ logarithmically growing Candida cells, which were suspended in physiological sodium chloride solution. The animals are treated orally one hour before and seven hours after the infection, with, in each case, 50-100 mg of the preparation/kg of body weight.

Result:

Untreated animals died 3 to 6 days after infection. The survival rate on the 6th day after infection was about 5% in the case of the untreated control animals.

In this experiment, the compounds according to the invention prove to have a very good action.

EXAMPLE C

Antimicrobial in vivo Activity (Local) Using the Model of Experimental Trichophytosis of Guineapigs Description of the experiment:

White guineapigs of the Pirbright-white strain were infected on their shaven, non-scarified backs with a microconidia and macroconidia suspension of Trichophyton mentagrophytes.

Starting on the 3rd day after infection, the infected animals were treated locally once daily with a 1% strength solution of the preparations according to the invention (in dimethylsulphoxide:glycerol=1:4).

Result:

In the case of untreated animals, the typical pattern of dermatophytosis with reddening, scaling and loss of hair up to total integumentary defect at the point of infection develops within 12 days after infection.

In contrast, for example, compounds of Examples 1 and 3 according to the invention exhibited a good action, that is to say only slight reddening and isolated scaling.

The following Examples illustrate processes for the preparation of compounds used according to the present invention.

EXAMPLE 1

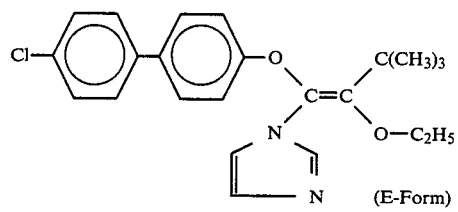

6 g of potassium hydroxide, dissolved in a little water, are added dropwise to 36.85 g (0.1 mole) of 1-(4'-chloro-4-biphenylyloxy)-3,3-dimethyl-1-(imidazol-1-yl)-butan-2-one in 50 ml of dimethylsulphoxide. The mixture is subsequently stirred for a short time and 16 g (0.11 mole) of diethyl sulphate are then added dropwise. During this addition, the temperature of the reaction mixture is kept at about 40° C. and thereafter it was kept at 80° C. for ½ hour. It was allowed to cool, water is added and the crystalline precipitate is filtered off and recrystallised from petroleum ether. 22 g (50% of theory) of (E)-1-(4'-chloro-4-biphenylyloxy)-3,3-dimethyl-2-ethoxy-1-(imidazol-1-yl)-1-butene of melting point of 112°-113° C. are obtained.

The following examples of the general formula

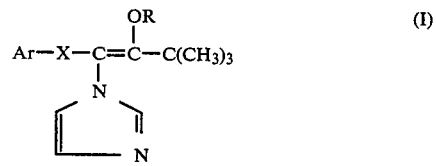

could be obtained in a corresponding manner:

| Example No: | Ar | X | R | Melting point: (°C.) |
|---|---|---|---|---|
| 2 | Cl—⟨phenyl⟩— | O | C₂H₅ | 94–95 (E-Form) |
| 3 | Cl—⟨phenyl⟩—⟨phenyl⟩— | O | CH₃ | 139–42 (E-Form) |

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to a warm-blooded animal is converted in the patient's body to the active compound.

What is claimed is:

1. A method of combating mycoses in warm-blooded animals which comprises administering to the animals an antimycotically, effective amount of a compound which is an imidazolylenol ether of the formula

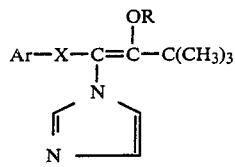

a physiologically acceptable acid addition salt or metal salt complex thereof,
in which
    Ar represents a phenyl or naphthyl radical optionally substituted by halogen; alkyl with 1 to 6 carbon atoms; alkoxy with 1 to 4 carbon atoms; halogenoalkyl with 1 to 4 carbon atoms and 1 to 5 halogen atoms; nitro, cyano; or phenyl which is optionally substituted by halogen,
    R represents an alkyl group with 1 to 4 carbon atoms, and
    X represents an oxygen atom or a methylene radical, either alone or in admixture with an inert pharmaceutical carrier on in the form of a medicament.

2. A method according to claim 1 in which the active compound is administered in an amount of 50 to 200 mg per kg body weight per day.

3. A method according to claim 1 in which the active compound is administered parenterally.

* * * * *